US00PP15815P2

(12) United States Plant Patent
Tristram

(10) Patent No.: US PP15,815 P2
(45) Date of Patent: Jun. 28, 2005

(54) ***AJUGA* PLANT NAMED 'BLACK SCALLOP'**

(50) Latin Name: *Ajuga reptans*
Varietal Denomination: Black Scallop

(76) Inventor: Michael Tristram, Stable Cottage, Binsted, Arundel, W. Sussex BN18 0LL (GB)

( * ) Notice: Subject to any disclaimer, the term of this patent is extended or adjusted under 35 U.S.C. 154(b) by 61 days.

(21) Appl. No.: 10/792,140

(22) Filed: Mar. 4, 2004

(51) Int. Cl.[7] ..... A01H 5/00
(52) U.S. Cl. ..... Plt./373
(58) Field of Search ..... Plt./373

*Primary Examiner*—Kent Bell

(57) ABSTRACT

A new and distinct cultivar of *Ajuga* named 'Black Scallop' that is characterized by dense compact habit, large round dark maroon-purple leaves and fragrant dark violet flowers. In combination these traits set 'Black Scallop' apart from all other existing varieties of *Ajuga* known to the inventor.

2 Drawing Sheets

Genus: *Ajuga.*
Species: *reptans.*
Denomination: Black Scallop.

BACKGROUND OF THE INVENTION

The present invention relates to a new and distinct cultivar of carpet bugle that is grown for use as an ornamental groundcover for the landscape. The new cultivar is known botanically as *Ajuga reptans* and will be referred to hereinafter by the cultivar name 'Black Scallop'.

For approximately eight years prior to the selection of 'Black Scallop' as described below, the inventor had grown for sale as one year old plants the dark-leaved *Ajuga reptans* variety known as 'Braunherz' (unpatented). In common with inventor's commercial practice, in order to obtain and maintain a reliable source of clean stock plants of 'Braunherz', the inventor had established plants of 'Braunherz' in vitro in the inventor's nursery laboratory. In 1998, the inventor observed a single plant within a batch of plants that had been grown in pots in soil-based medium from the inventor's in vitro 'Braunherz' material. This single plant, 'Black Scallop', was a naturally occurring whole plant mutation that exhibited novel and attractive foliage characteristics which the inventor considered set it apart from 'Braunherz' and from other varieties of *Ajuga* known to the inventor. The inventor isolated, and in 2000 first asexually reproduced 'Black Scallop' using basal shoot cuttings. All of the resulting plants were grown to maturity and the inventor determined that 'Black Scallop' had remained stable and true to type. 'Black Scallop' has remained stable and true to type through subsequent generations of asexual reproduction.

'Black Scallop' is a perennial ground cover with dark violet flowers and a mat of dark maroon-purple leaves. The parent plant is *Ajuga reptans*' 'Braunherz' which is considered by the inventor to be the closest comparison plant to 'Black Scallop'. The foliage of 'Black Scallop' is larger and rounder and more uniformly dark than other medium-sized cultivars of dark-leaved *Ajuga* known to the inventor, including 'Braunherz'. The foliage of 'Black Scallop' is smaller than the large-sized cultivars of bronze-green-leaved *Ajuga* known to the inventor, including the cultivar *Ajuga* 'Catlin's Giant' (unpatented) which is typical of the type. When compared with 'Braunherz', 'Black Scallop' exhibits larger flowers and the whole plant exhibits greater heat tolerance, and greater resistance to powdery mildew.

SUMMARY OF THE INVENTION

The following traits have been repeatedly observed and represent the distinguishing characteristics of the new *Ajuga* cultivar 'Black Scallop'. These traits in combination, distinguish 'Black Scallop' from all other varieties of *Ajuga* known to the inventor. 'Black Scallop' has not been tested under all possible conditions. Phenotypic differences might occur with variations in environmental, climatic, and cultural conditions without any variance in genotype.

1. The new *Ajuga* cultivar 'Black Scallop' is a perennial ground cover.
2. The new *Ajuga* cultivar 'Black Scallop' exhibits a dense compact habit.
3. The new *Ajuga* cultivar 'Black Scallop' exhibits dark maroon-purple leaves.
4. The leaves of the new *Ajuga* cultivar 'Black Scallop' exhibit scalloped margins.
5. The new *Ajuga* cultivar 'Black Scallop' exhibits large, thick reddish stems.
6. The new *Ajuga* cultivar 'Black Scallop' is resistant to powdery mildew, and heat tolerant.
7. The new *Ajuga* cultivar 'Black Scallop' exhibits short internodes.
8. The new *Ajuga* cultivar 'Black Scallop' exhibits large dark violet flowers from spring to early summer.
9. The new *Ajuga* cultivar 'Black Scallop' exhibits short flower stalks that produce inflorescences borne above the foliage.
10. A mature (second season) plant of the new *Ajuga* cultivar 'Black Scallop' measures 30 cm to 40 cm in width and approximately 20 cm in height when grown in the ground or in a 2-liter container.
11. The new *Ajuga* cultivar 'Black Scallop' is hardy to USDA Zone 6.
12. The new *Ajuga* cultivar 'Black Scallop' is propagated by tip cuttings and division.

BRIEF DESCRIPTION OF THE DRAWINGS

The accompanying color drawings illustrate the overall appearance of the new *Ajuga* cultivar 'Black Scallop', showing the colors as true as it is reasonably possible to obtain in colored reproductions of this type. Colors in the photographs may differ from the color values cited in the detailed botanical description, which accurately describe the actual colors of the new variety 'Black Scallop'.

Figure 1:
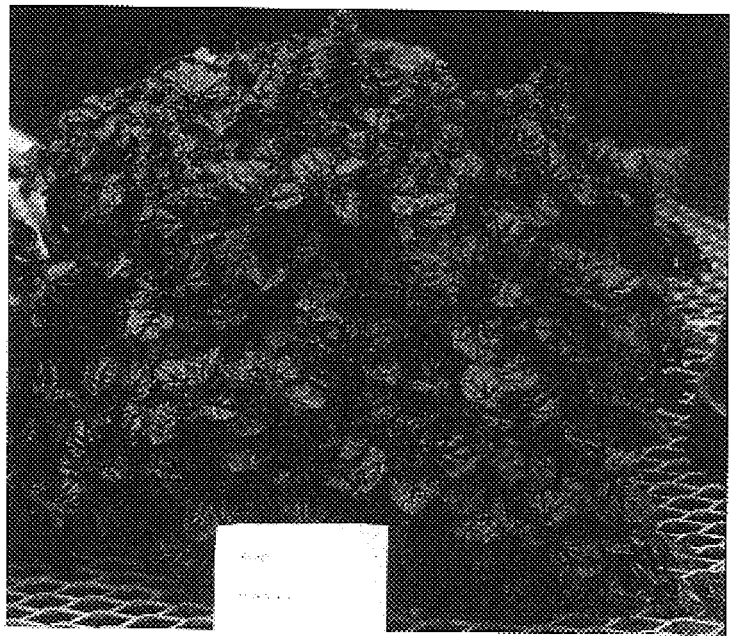
FIG. 1 illustrates an entire plant of 'Black Scallop' which is coming into bloom in its second year of growth in a 2 liter container. The plant has been grown outside for approximately eighteen months in a frost-free environment.
Figure 2:
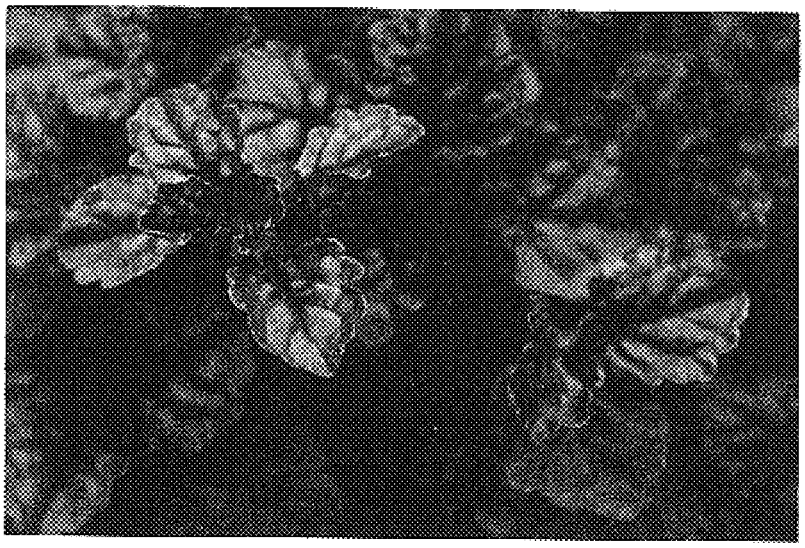
FIG. 2 illustrates a close-up view of the foliage of 'Black Scallop'.

The drawings are made using conventional photographic techniques and although flower and foliage colors in the photographs may differ from the actual colors due to light reflectance, they are as accurate as conventional photography can portray.

BOTANICAL DESCRIPTION OF THE PLANT

The following is a detailed botanical description of the new *Ajuga* cultivar 'Black Scallop'. Observations, measurements, values and comparisons were collected in Arroyo Grande, Calif. from plants in their second season of growth in 2-liter containers that were grown out-of-doors in a frost-free environment. Color determinations are made in accordance with 2001 Edition of the Colour Chart of The Royal Horticultural Society, London England, except where general color terms of ordinary dictionary significance are used. The growing requirements of the new variety are similar to the species and there are no growing problems known to the inventor.

Botanical classification: *Ajuga* 'Black Scallop'.
Common name: Carpet bugle.
Parentage: *Ajuga* 'Black Scallop' is a naturally occurring whole plant mutation of the following parent plant:
*Parent plant.*—*Ajuga reptans* 'Braunherz'.
Propagation method: Propagation is accomplished by division and vegetative tip cuttings.
Rooting habit: Fine and fibrous.
Time to develop roots: Approximately 30 days are required to develop roots from an initial tip cutting.
Crop time (from a rooted cutting): Six months are required to achieve a finished 4 inch or 1 quart of 10 cm container. Eighteen months are required to achieve a finished 2-liter container.
Plant habit: Dense, compact habit.
Commercial classification: Groundcover.
Use: Ornamental for the landscape.
Type: Perennial.
Growth rate: Moderate to vigorous.
Height of plant (second year): Approximately 20 cm.
Width of plant (second year): From 30 cm to 40 cm.
Hardiness: USDA Zone 6.
Cultural requirements: Full sun, regular water and moisture retentive soil.
Pest and disease resistance: Resistant to powdery mildew, and tolerant of heat.
Stem:
*Branching habit.*—Basal.
*Stem color.*—184A.
*Stem shape.*—Tetragonal.
*Stem width.*—0.50 cm. in width.
*Stem length.*—10 cm. in length.
*Internode length.*—2 cm. between nodes.
*Stem surface.*—Mostly glabrous with 2 longitudinal ridges each on opposite sides of stem.
Foliage:
*Leaf arrangement.*—Opposite.
*Leaf division.*—Simple.
*Leaf shape.*—Orbicular.
*Mature leaf length.*—Average length is 5.75 cm.
*Mature leaf width.*—Average width is 5.75 cm.
*Immature leaf length.*—Average length is 2.75 cm.
*Immature leaf width.*—Average width is 2.75 cm.
*Leaf apex.*—Obtuse.
*Leaf base.*—Cordate.
*Quantity of leaves.*—Average of 12 to 15 leaves per stem.
*Leaf venation pattern.*—Palmate.
*Vein color* (*adaxial surface*).—186A.
*Vein color* (*abaxial surface*).—138C.
*Margin type.*—Crenate or scalloped.
*Leaf appearance* (*adaxial and abaxial surfaces*).—Semi-glossy.
*Leaf surface* (*adaxial*).—Rugose or puckered surface and sparsely puberulent.
*Leaf surface* (*abaxial*).—Glabrous depressions.
*Leaf attachment.*—Petiolate.
*Petiole shape.*—Sulcate.
*Petiole dimensions* (*mature leaves*).—On an individual plant petiole dimensions are 0.75 cm. in width and range from 2 cm–4 cm. in length.
*Petiole dimensions* (*immature leaves*).—On an individual plant petiole dimensions are 0.25 cm. in width and range from 0.75–1.75 cm. in length.
*Petiole surface* (*adaxial and abaxial surfaces*).—Glabrous.
*Mature petiole color* (*adaxial surface*).—Individual colors N186B and N186C are present on each individual petiole.
*Mature petiole color* (*abaxial surface*).—138A.
*Immature petiole color* (*adaxial surface*).—A combination of N186B and N138A is present on each individual petiole.
*Immature petiole color* (*abaxial surface*).—138B.
*Mature leaf color* (*adaxial surface*).—A combination of N186B and 189A is present on each individual leaf.
*Mature leaf color* (*abaxial surface*).—138A.
*Immature leaf color* (*adaxial surface*).—A combination of 139A and N186A is present on each leaf.
*Immature leaf color* (*abaxial surface*).—138A.
*Leaf fragrance.*—None present.
Flower:
*Flower shape.*—Tubular to ampliate.
*Flower color.*—86B.
*Bud dimensions.*—2.50 mm. in diameter and 3 mm in length.
*Shape of corolla tube.*—Tubular in shape.
*Surface of corolla tube* (*inner and outer surfaces*).—Puberulent.
*Corolla tube color* (*inner and outer surfaces*).—86B.
*Flower depth.*—15 mm. in depth.
*Flower width.*—8 mm. in diameter.
*Corolla tube length.*—6 mm. in length.
*Corolla tube diameter.*—3 mm. in diameter.
*Number of petals.*—Three in number.
*Petal margins.*—Entire.
*Petal apex.*—Rounded.

*Petal dimensions.*—4 mm. in width and 9 mm. in length.
*Color of petals* (*adaxial surface*).—86B.
*Color of petals* (*abaxial surface*).—N88C.
*Petal surface* (*adaxial surface*).—Glabrous.
*Petal surface* (*abaxial surface*).—Lanate.
*Petals fused or unfused.*—Petals are basally fused.
*Shape of petals.*—Closet to spatulate.
*Flowering season.*—Spring to early summer.
*Aspect.*—Facing outward and upward.
*Inflorescence.*—Axillary cyme.
*Flower arrangement.*—Flowers are arranged in whorls.
*Quantity of flowers.*—An average of 50 flowers per 2-liter container.
*Peduncle dimensions.*—3 mm. in width by 5 mm. in length.
*Peduncle shape.*—Terete in shape.
*Peduncle surface.*—Lanate.
*Peduncle color.*—138D.
*Calyx shape.*—Cupule.
*Calyx dimensions.*—5 mm. in length and 6 mm. in diameter.
*Calyx color* (*outer surface*).—138D.
*Calyx surface* (*outer surface*).—Lanate.
*Calyx color* (*inner surface*).—138D.
*Calyx surface* (*inner surface*).—Lanate.
*Number of sepals.*—Five in number.
*Fused or unfused.*—Unfused.
*Sepal apex.*—Acute.
*Sepal base.*—Rounded.
*Sepal margins.*—Entire.
*Sepal shape.*—Ovate.
*Sepal surfaces* (*adaxial and abaxial*).—Lanate.
*Sepal color* (*adaxial and abaxial surfaces*).—138D.
*Bract number.*—Two bracts per axillary cyme.
*Bract apex.*—Obtuse.
*Bract base.*—Rounded.
*Bract shape.*—Orbicular.
*Bract color* (*adaxial and abaxial surfaces*).—Colors N186B and 138A are both individually present on an individual bract.
*Bract dimensions.*—One individual bract is 1.25 cm. in width and 1.25 cm. in length.
*Bract surfaces* (*adaxial and abaxial surfaces*).—Pubescent.
*Bract margins.*—Entire.
*Flower fragrance.*—Scented perfume fragrance.

Reproductive organs:
*Stamens.*—Four in number.
*Stamen length.*—8 mm. in length.
*Stamen color.*—84D.
*Anther dimensions.*—1 mm. in length and 1 mm. in width.
*Anther color.*—162B.
*Pollen color.*—162B.
*Quantity of pollen.*—Small amount.
*Pistil.*—One in number.
*Pistil shape.*—Filiform.
*Pistil length.*—12 mm. in length.
*Pistil color.*—N88A.
*Pistil surface.*—Glabrous.
*Ovary position.*—Superior.
*Ovary shape.*—Globular.
*Ovary dimensions.*—2 mm. in height and 2 mm. in diameter.
*Ovary color.*—138C.

Seed: No seed has been observed to date.

It is claimed:

1. A new and distinct variety of *Ajuga* plant named 'Black Scallop' as illustrated and described herein.

* * * * *